United States Patent
Herve et al.

(10) Patent No.: US 7,133,494 B2
(45) Date of Patent: Nov. 7, 2006

(54) METHOD FOR RADIOLOGICAL EXAMINATION OF AN OBJECT

(75) Inventors: Lionel Herve, Bourg-lis- Valence (FR); Christine Robert-Coutant, St. Martin d'uriage (FR)

(73) Assignee: Commissariat a l'Energie Atomique, Paris (FR)

( * ) Notice: Subject to any disclaimer, the term of this patent is extended or adjusted under 35 U.S.C. 154(b) by 0 days.

(21) Appl. No.: 10/612,099

(22) Filed: Jul. 2, 2003

(65) Prior Publication Data
US 2006/0045233 A1    Mar. 2, 2006

(30) Foreign Application Priority Data
Jul. 5, 2002 (FR) .................................. 02 08513

(51) Int. Cl.
*G01N 23/087* (2006.01)
(52) U.S. Cl. .................... 378/98.9; 378/5; 378/18; 378/53
(58) Field of Classification Search ............. 378/5, 378/16, 98.9, 98.11, 8, 53, 57
See application file for complete search history.

(56) References Cited

U.S. PATENT DOCUMENTS

| 3,965,358 A | | 6/1976 | Macovski ........................ 378/5 |
| 4,029,963 A | * | 6/1977 | Alvarez et al. ................. 378/5 |
| 5,123,037 A | * | 6/1992 | Picard et al. .............. 378/98.2 |
| 5,247,559 A | * | 9/1993 | Ohtsuchi et al. ............. 376/53 |
| 6,370,223 B1 | * | 4/2002 | Gleason et al. ................ 375/58 |
| 6,449,334 B1 | * | 9/2002 | Mazess et al. ................. 378/53 |
| 6,574,302 B1 | * | 6/2003 | Adriaansz ..................... 378/54 |
| 6,678,350 B1 | * | 1/2004 | Dolazza et al. ............ 378/98.9 |
| 6,735,273 B1 | * | 5/2004 | Flohr et al. ..................... 378/5 |
| 6,754,298 B1 | * | 6/2004 | Fessler ........................... 378/4 |

OTHER PUBLICATIONS

J. Swanpalmer, R. Kullenberg and T. Hansson, "Measurement of Bone Mineral Using Multiple-Energy X-Ray Absorptiometry", Phys. Med, Biol. 43 (1998), 379-387.
C. R. Coutant, V. Moulin, R. Sauze, P. Rizo and J.M. Casgrande, "Estimation of the Matrix Attenuation in Heterogeneous Radioactive Waste Drums Using Dual-Energy Computed Tomography", Nuclear Instruments & Methods in Physics Research, A 422(1999), 949-956.

* cited by examiner

*Primary Examiner*—Allen C. Ho
(74) *Attorney, Agent, or Firm*—Pearne & Gordon LLP

(57) ABSTRACT

The invention relates to a method for x-ray examination of an object where two categories of materials are taken into consideration, comprising: the use of broad spectrum x-rays; measurements of the x-rays by bands of the spectrum; expressions ($\hat{M}$) of thicknesses or masses of the two categories of materials passed through by the x-rays, the expressions ($\hat{M}$) being functions of at least two of the measurements ($mes_k$) and coefficients (A); and applying a selection criterion from among the expressions ($\hat{M}$) to deduce from this an expression (final $\hat{M}$) considered true; characterized in that the selection criterion comprises a combination (f) of the expressions with weighting factors (a), and a calculation of the weighting factors such that the combination has minimal variation according to variations of the measurements.

13 Claims, 2 Drawing Sheets

METHOD FOR RADIOLOGICAL EXAMINATION OF AN OBJECT

This invention relates to a method for multiple-energy x-ray examination of an object.

Radiological processes consist of having an x-ray pass through an object to be analyzed in order to deduce the distribution of various categories of materials in this object, absorbing the x-ray in different ways. A very common application is osteodensitometry, where the mass and density of bone tissue in a patient are analyzed, distinguishing these tissues from soft tissues.

It is typical to use a broad spectrum of x-rays and to divide it into bands measured separately by respective measuring channels. Since the coefficients factors of absorption or attenuation of the x-ray by a given tissue category differ for each of the bands, the theoretical problem comes down to solving a system of equations, the number of which is the same as that of the measuring bands and each comprising two unknowns (the thicknesses and the masses of soft and bony tissue passed through). The problem becomes possible to solve after calibrating, achieved by having the x-ray pass through various standards provided with known thicknesses of materials with absorptive properties similar to those of the measuring material, in particular plexiglass and hydroxyapatite to simulate the soft tissue and the bony tissue. The mathematical parameters of a model linking the attenuation measurements to the thicknesses of the materials can than be calculated.

It should be noted that in actual fact, the human body contains three main categories of tissue: bony tissue, lean tissue and fatty tissue, but only two of them are generally taken into consideration due to the difficulty of distinguishing these three categories in the measurements, such that lean and fatty tissue are deliberately taken into consideration together. Other methods are then applied to distinguish their proportions in the soft tissue.

The breadth of the spectrum makes it possible to have a must larger number of measuring bands than would be needed to obtain a solution, and to use all of them to obtain more precise results by making use of all of the absorption data obtained. In the article "Measurement of bone material using a multiple-energy x-ray absorptiometry," by J. Swanpalmer, R. Kullenberg, T. Hansson, Phys. Med. Biol., Vol. 43, 1997: pp. 379–387, where there are 23 measuring bands and where the three categories of tissue are taken into consideration, it is proposed to combine the measuring groups in threes in every way possible to obtain 1771 (23×22×21/2×3) systems of three equations with three unknowns that yield as many groups of results. A criterion of choice should then be applied. The authors advise choosing as the true result the one that is at the mean value, or the median value, for the most important parameter, which can be the bony mass passed through.

Contrary to the above recommendation, the authors take into consideration the three categories of tissue. That does not call into question the validity of their method, provided the patient is exposed to a much stronger radiation intensity to reduce the uncertainties of the measurements to acceptable proportions. One could also simply modify their method and apply it to measurements on only two tissues, or more generally speaking, two categories of materials. However, this method is flawed in that it does not take into account the noise on the measurements, and it thus yields results with noise.

The purpose of the invention is to perfect such methods by combining numerous results, and it comprises improving the result selection criteria. More precisely, in its most general form it relates to a method for radiological examination of an object in which at least two categories of materials are taken into consideration, comprising: the use of broad spectrum x-rays; measurements of the x-rays by bands of the spectrum; expressions ($\hat{M}$) of thicknesses or masses of the two categories of materials passed through by the x-rays, the expressions ($\hat{M}$) being functions of at least two of the measurements ($mes_k$) and coefficient (A); and applying a selection criterion from among the expressions ($\hat{M}$) to deduce from it an expression (final $\hat{M}$) considered true; characterized in that the selection criterion comprises a combination (f) of the expressions with weighting factors (a), and a calculation of weighting factors such that the combination has minimal noise (minimal variance in mathematical language) calculated according to the noise levels on the measurements (variance on the measurements).

The invention will now be described referring to the figures.

Figure 1:
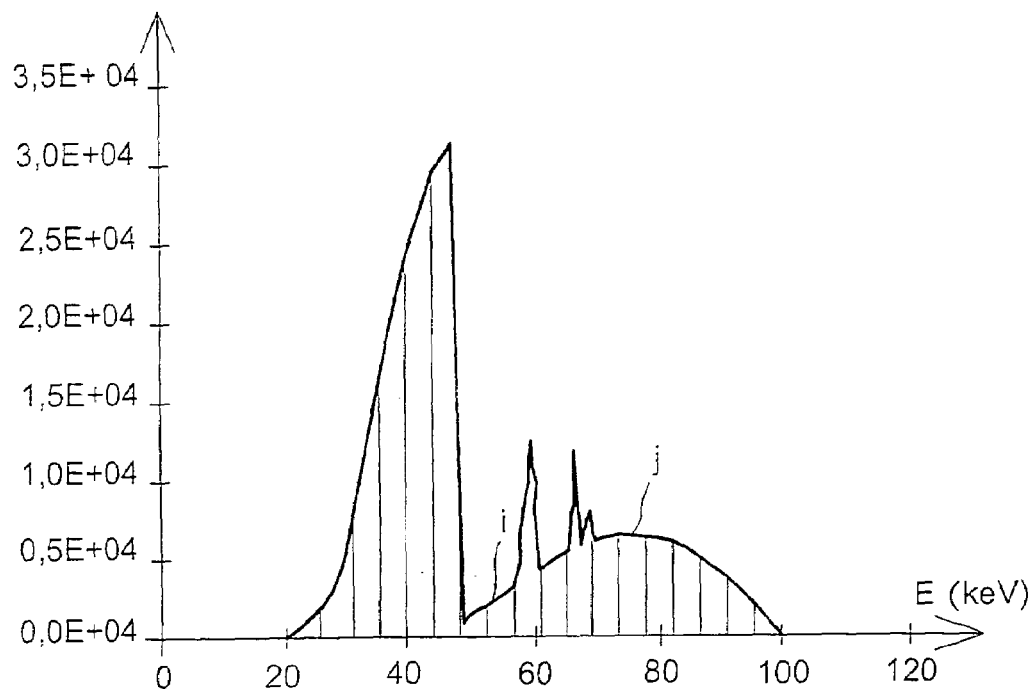
FIG. 1 is a spectrum view.
Figure 2:
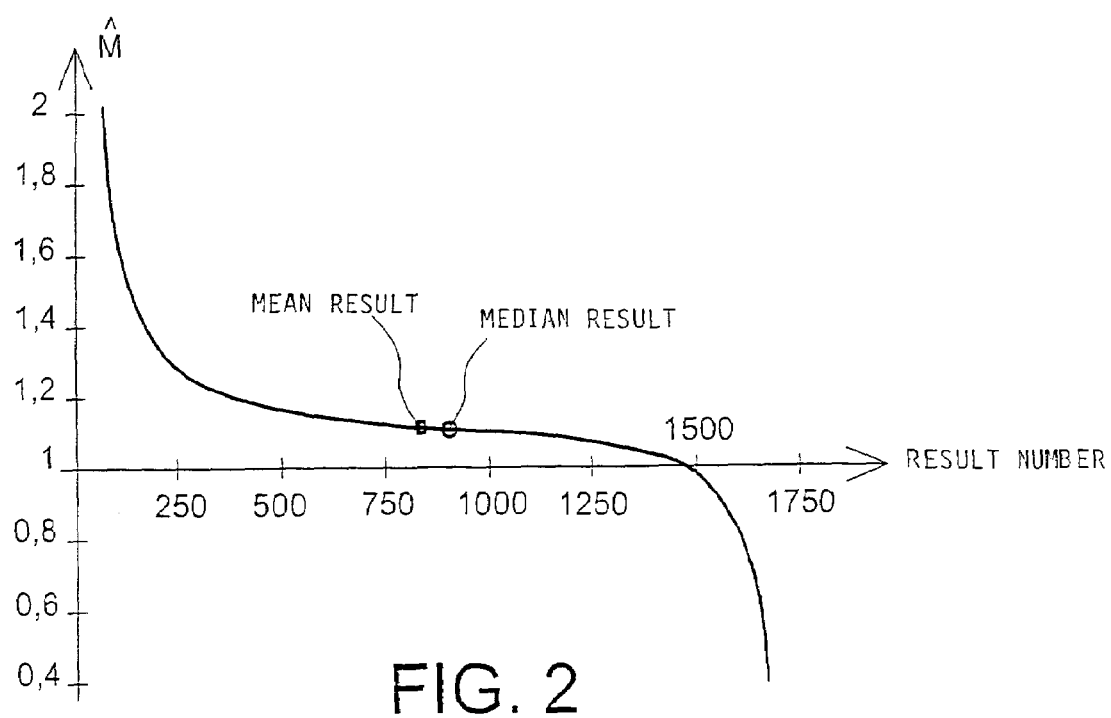
FIG. 2 is a distribution of results.
Figure 3:
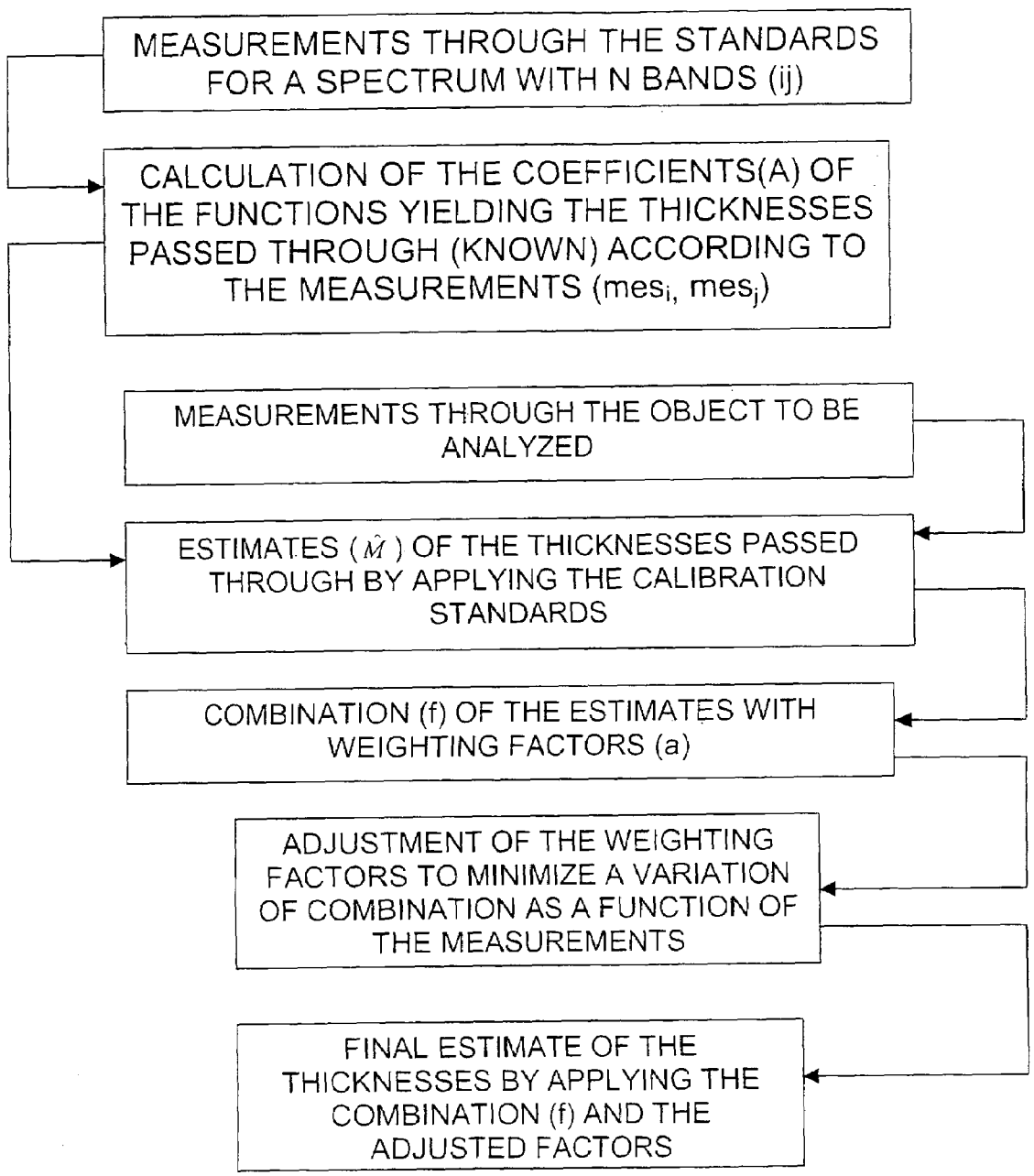
FIG. 3 is a flowchart summarizing the invention, which can be referred to throughout the following description.

The attenuation of the x-rays can be expressed as a function of the thicknesses passed through for each of the materials of indicators x and y, or of their masses M (density per surface unit) in the direction of the x-rays. The spectrum of measurements in FIG. 1 is divided into N bands generally marked by indicators i and j. The attenuations will vary in each of the bands according to variable absorption coefficients for the two materials. If we call $mes_i$ or $mes_j$ the measurements for a band of energy i or j, the masses passed through $M_x$ and $M_y$ can each also be expressed by the general formula $$(\hat{M})=A_1+A_2 \cdot mes_i+A_3 \cdot mes_j+A_4 \cdot mes_i^2 + A_5 \cdot mes_j^2 + A_6 \cdot mes_i \cdot mes_j$$

The measurements considered in this example being attenuation measurements, we will have for each measurement channel i (corresponding to a band of the spectrum) the relation $mes_i = \ln(noi/ni)$ where noi is the number of photons arriving on the object and ni the number of photons having passed through the object. Since the non-linearity of the functions $M_x$ and $M_y$ as a function of the measurements is slight in practical reality, one can make use of this second degree polynomial function that comprises six coefficients $A_1$ through $A_6$. The degree of the polynomial can be adjusted depending on the problem. For example, to analyze objects made of materials having atomic numbers higher than that of biological tissue, as in non-destructive monitoring for examining a metal object, the measurements considered in this example being attenuation measurements, we will have for each measurement channel i (corresponding to a band of the spectrum) the relation $mes_i = \ln(noi/ni)$ where noi is the number of photons arriving on the object and ni the number of photons having passed through the object.

These coefficients can be found in a phase of calibration through standards, sometimes called phantoms or wedges in the prior art, consisting of shaped parts with known, differing thicknesses made of materials simulating with their attenuation properties the materials of the object that will actually be measured. Each of these standards is thus radiated with the x-rays for a long period, making it possible to reduce the noise's influence on the measurements. The spectrum measured for each of the standards still yields N measurements resulting from the decomposition of the spectrum into as many bands. By then combining two series of measurements i and j taken for two bands N for each of the standards, the coefficients A are analyzed to adjust the functions $M_x$ and $M_y$ to the measurements. In this case, where there are six coefficients A for each of the two functions, and where the combinations of two bands of measurements are being considered, the measurements for each of the bands will have to be for six standards in order to produce a unique solution. More numerous standards may also be used to improve precision on the solution. An error function minimizing will then be applied.

This determining of coefficients A is repeated for various combinations of pairs of measurements. This was still the case in the above-mentioned previous article; however, it was noted that it was pointless to do all of the combinations, numbering Nx(N−1)/2, to fully utilize the measurements and that (N−1) combinations were actually enough to gather all of the data.

A preferred method consists of choosing in the beginning the band of measurements with the least noise (for example the one that has the greatest signal n—number of photons at reception) and successively combining it with each of the other bands of measurements for the combinations. One finally obtains (N−1) estimates of the two functions $M_x$ and $M_y$, which are noted $\hat{M}_1, \hat{M}_2, \ldots, \hat{M}_{N-1}$ for each of these two functions.

At this stage of the process, the functions $M_x$ and $M_y$ representing the lengths passed through in two materials representing bony tissue and soft tissue can be converted to functions $M_u$, $M_v$ and $M_w$ representing equivalent lengths passed through in the bony tissue, lean tissue and fatty tissue by combining linearly $M_x$ and $M_y$ in three different ways determined by experiment. This conversion method is independent of the invention and already ready known in the prior art.

Since there is no reason to prefer either of these $\hat{M}$ estimates, a selection criterion must be applied to obtain the final $\hat{M}$ estimate that will be considered true. In the previous article, one of the expressions obtained was directly selected according to a criterion of classification (the mean result) or median of the values considered by the expressions for one of the results. In the invention, the $\hat{M}$ expressions will be combined; e.g. linearly according to the final $\hat{M}$ formula=$(a_1 \hat{M}_1)+(a_2 \hat{M}_2)+\ldots+(a_{N-1} \hat{M}_{N-1})$ while minimizing the noise; the coefficients $a_1$, etc. have a sum equal to the unit (a1+ a2+ ... +aN−1=1).

For each measurement channel, the noise on the number of photons follows a Poisson statistical law, the result of which is independent for each of the channels. The covariance matrix of the N−1 results can be expressed according to the formula $$\Gamma_{ij} = \sum_{k=1}^{N-1} \frac{\partial M?_1}{\partial mes_k} \frac{\partial M?_f}{\partial mes_k} \frac{1}{N_k}$$

The variance on the linear combination yielding final $\hat{M}$ is expressed by the formula:

$f=(a_1, \ldots, a_{N-1}) \cdot \Gamma^{-1} (a_1, \ldots, a_{N-1})$;

this quantity f attains an optimal value when its derivative according to all of the variables is null, that is, the noise's influence is minimized, i.e., $$\begin{cases} \partial f / \partial a_1 = 0 \\ \partial f / \partial a_2 = 0 \\ \ldots \\ \partial f / \partial a_{N-1} = 0 \end{cases}$$

The numerical resolution of this system provides the coefficients $a_1$, $a_2$, etc. N final $\hat{M}$, that is, the masses passed through in the two categories of materials.

These are the operations completed in the invention; it should be noted that the measurements ($mes_x$) used in the formula yielding $\Gamma_{ij}$ and so forth are the measurements carried out through the actual object to be analyzed, but not those that were made by calibration to determine the coefficients A of the functions $\hat{M}$.

The invention makes it possible to avoid the dilemma of prior methods in which part of the measurement energy was given up or, on the contrary, measurements that barely differed were accepted: it indeed uses the entire spectrum, but divides it into bands that are numerous enough to enable the measurement of each one to be usefully compared to other measurements made on distant bands. It thereby makes it possible, among other advantages, to analyze lean organisms as well as fatty ones.

Lastly, the invention can be broadened to a greater number of materials than two, which can be advantageous in particular for imaging processes with contrast products, where three variables must be considered or for checking baggage (searching for explosives); and it can be applied when considering combinations of the $\hat{M}$ functions other than linear ones, Applications of the invention are:
osteodensitometry
obtaining the density of bone mass
obtaining body composition (fat mass, lean mass)
food-processing inspection, e.g. detecting bone fragments in meat or detecting pieces of glass in meals being served,
baggage inspection; searching for explosives, illegal products (weapons, food, drugs, . . . ).

The invention claimed is:

1. A method for examining an object comprising at least two categories of materials in order to determine a value of a physical parameter of each of said materials, the method comprising the steps of:
    applying radiation through the object, the radiation belonging to a broadband energy spectrum;
    taking a plurality, of measurements of the radiation after having passed through the object, said measurements being taken at respective energy bands in said spectrum;
    selecting a plurality of pairs of said energy bands;
    defining, for each of said materials and each of said pairs, a function of an intermediate parameter ($\hat{M}$) based on the measurements in the energy bands in the pair and on coefficients obtained in a previous calibration, each of said intermediate parameters being an estimation of the value of the physical parameter for one of said materials, and calculating values of said intermediate parameters;
    defining a weighted sum of said intermediate parameters for each of said materials, the intermediate parameters ($\hat{M}$) being weighted by weighting coefficient;
    calculating values of said weighting coefficients by minimizing a variance of said weighted sum; and calculating, for each of the materials, said value of said physical parameter with the weighted sum based on said values of said weighted coefficients and said values of said intermediate parameters.

2. A method according to claim 1, wherein said variance is minimized when a variation of a value of the weighted sum is minimized according to variations of values of said measurements.

3. A method according to claim 2, wherein said variations of values of said measurements are computed according to a statistical law.

4. A method according to claim 3, wherein said statistical law entails variances of said measurements, and said variance of said weighted sum is computed from said variances of said measurements.

5. A method according to claim 3, wherein said statistical law is a Poisson law applied on a number of photons of the radiation.

6. A method according to claim 1, wherein said pairs are equal in number to the number of said energy bands less one.

7. A method according to claim 6, wherein said pairs each comprise the same energy band.

8. A method according to claim 1, wherein said functions of said intermediate parameters are polynomials.

9. A method according to claim 8, wherein said polynomials comprise one constant term, two linear terms of said measurements, two quadratic terms of said measurements, and one term proportional to both said measurements.

10. A method according to claim 1, wherein said variance is computed with a covariance matrix expressing derivatives of said intermediate parameters with respect to said measurements.

11. A method according to claim 1, wherein the calibration is done with phantoms made of material having known thicknesses and properties similar to the materials of the object with respect to irradiation by said radiation.

12. A method according to claim 1, wherein said materials are bone tissue and soft tissue.

13. A method for examining an object comprising at least two categories of materials in order to determine a value of a physical parameter of each of said materials, the method comprising the steps of:

applying radiation through the object, the radiation belonging to a-broadband energy spectrum;

taking a plurality of measurements of the radiation after having passed through the object, said measurements being taken at respective energy bands in said spectrum;

selecting a plurality of pairs of said energy bands, wherein said pairs are equal in number to the number of said energy bands less one, and wherein each one of said pairs have the same energy band;

defining, for each of said materials and each of said pairs, a function of an intermediate parameter ($\hat{M}$) based on the measurements in the energy bands in the pair and on coefficients obtained in a previous calibration using phantoms made of material having known thicknesses and properties similar to the materials of the object with respect to irradiation by said radiation, each of said intermediate parameters being an estimation of the value of the physical parameter for one of said materials, and calculating values of said intermediate parameters, wherein said functions of said intermediate parameters are polynomials comprising one constant term, two linear terms of said measurements, two quadratic terms of said measurements, and one term proportional to both said measurements;

defining a weighted sum of said intermediate parameters for each of said materials, the intermediate parameters ($\hat{M}$) being weighted by weighting coefficient;

calculating values of said weighting coefficients by minimizing a variance of said weighted sum; and calculating, for each of the materials, said value of said physical parameter with the weighted sum based on said values of said weighted coefficients and said values of said intermediate parameters.

* * * * *

UNITED STATES PATENT AND TRADEMARK OFFICE
CERTIFICATE OF CORRECTION

PATENT NO.         : 7,133,494 B2
APPLICATION NO. : 10/612099
DATED              : November 7, 2006
INVENTOR(S)        : Herve et al.

It is certified that error appears in the above-identified patent and that said Letters Patent is hereby corrected as shown below:

Column 3, starting at Line 55 and ending at Line 59, please delete the formula:

and insert therefor:

$$-- \Gamma_{ij} = \sum_{k=1}^{N-1} \frac{\partial \hat{M}_I}{\partial mes_k} \bullet \frac{\partial \hat{M}_J}{\partial mes_k} \bullet \frac{1}{N_k} --$$

Signed and Sealed this

Seventh Day of August, 2007

JON W. DUDAS
*Director of the United States Patent and Trademark Office*